(12) United States Patent
Garcia et al.

(10) Patent No.: US 8,618,321 B2
(45) Date of Patent: Dec. 31, 2013

(54) DERIVATIVES OF TRIS(2-HYDROXYPHENYL)METHANE, THEIR PREPARATION AND USE

(75) Inventors: Marta Reinoso Garcia, Dossenheim (DE); Günter Oetter, Frankenthal (DE); Vandana Kurkal-Siebert, Heidelberg (DE); Björn Heinz, Mannheim (DE); Christian Bittner, Bensheim (DE); Markus Hansch, Speyer (DE); Roman Benedikt Raether, Speyer (DE)

(73) Assignee: BASF SE, Ludwigshafen (DE)

( * ) Notice: Subject to any disclaimer, the term of this patent is extended or adjusted under 35 U.S.C. 154(b) by 79 days.

(21) Appl. No.: 13/111,298

(22) Filed: May 19, 2011

(65) Prior Publication Data

US 2011/0288322 A1    Nov. 24, 2011

Related U.S. Application Data

(60) Provisional application No. 61/346,482, filed on May 20, 2010.

(51) Int. Cl.
| | |
|---|---|
| C07C 41/03 | (2006.01) |
| C07C 317/16 | (2006.01) |
| C07C 43/205 | (2006.01) |
| C07C 39/16 | (2006.01) |

(52) U.S. Cl.
USPC ............................. 558/23; 568/640; 568/720

(58) Field of Classification Search
None
See application file for complete search history.

(56) References Cited

U.S. PATENT DOCUMENTS

| 5,741,947 | A | 4/1998 | Wolf et al. |
| 7,335,235 | B2 | 2/2008 | Ruland et al. |
| 7,461,694 | B2 | 12/2008 | Dahanayake et al. |
| 2005/0155762 | A1 | 7/2005 | Chen et al. |
| 2009/0155714 | A1 | 6/2009 | Lee et al. |

FOREIGN PATENT DOCUMENTS

| DE | 43 25 237 A1 | 2/1995 |
| DE | 102 43 361 A1 | 1/2004 |
| EP | 597 806 A1 | 5/1994 |
| WO | WO 2008/100436 | 8/2008 |

OTHER PUBLICATIONS

Mitra et al., caplus an 2007:1077766.*
U.S. Appl. No. 12/903,441, filed Oct. 13, 2010, Bittner et al.
U.S. Appl. No. 12/903,654, filed Oct. 13, 2010, Bittner et al.
U.S. Appl. No. 12/903,762, filed Oct. 13, 2010, Bittner et al.
U.S. Appl. No. 12/950,646, filed Nov. 19, 2010, Steiner et al.
U.S. Appl. No. 13/044,345, filed Mar. 9, 2011, Bittner et al.
U.S. Appl. No. 13/043,210, filed Mar. 8, 2011, Bittner et al.
U.S. Appl. No. 13/044,283, filed Mar. 9, 2011, Bittner et al.
U.S. Appl. No. 13/085,248, filed Mar. 9, 2011.
U.S. Appl. No. 13/091,677, filed Apr. 21, 2011, Bittner et al.
U.S. Appl. No. 13/093,356, filed Apr. 25, 2011, Bittner et al.
U.S. Appl. No. 61/251,310, filed Oct. 14, 2009, Bittner et al.
U.S. Appl. No. 61/251,314, filed Oct. 14, 2009, Bittner et al.
U.S. Appl. No. 61/251,315, filed Oct. 14, 2009, Bittner et al.
U.S. Appl. No. 61/312,292.
U.S. Appl. No. 61/312,294.
U.S. Appl. No. 61/312,299.
U.S. Appl. No. 61/312,302.
U.S. Appl. No. 61/315,051.
U.S. Appl. No. 61/325,051.
U.S. Appl. No. 61/327,118, filed Apr. 23, 2010, Bittner et al.
U.S. Appl. No. 61/327,124.
U.S. Appl. No. 61/394,369.
G. Casiraghi, G. Casnati and M. Cornia, Tetrahedron Letters, No. 9, 679-9,682 (1973).
M. B. Dinger and M. J. Scott describe in Chem. Commun., 1999, 2525/2526.
M. B. Dinger and M. J. Scott, Inorg. Chem. 2000, 39, 1238-1254.
M. B. Dinger and M. J. Scott, Inorg. Chem. 2001, 40, 1029-1036.
M. B. Dinger and M. J. Scott, Eur J. Org. Chem. 2000, 2467-2478.
K. Matloka, A. Gelis, M. Regalbuto, G. Vandegift and M. J. Scott, Dalton Trans., 2005, 3719-3721.
K. Matloka, A. Gelis, M. Regalbuto, G. Vandegift and M. J. Scott , Separation Science and Technology, 41, 2006, 2129-2146.
M. W. Peters, E. J. Werner and M. J. Scott, Inorg. Chem., 2002, 41, 1701-1716.
R. Mitra, M.W. Peters and M. Scott, Dalton Trans., 2007, 3924-3935.
H. Hoffmann et al., Adv. Colloid Interface Sci. 1982, 17, 275-298.
M. R. Rojas et al., Journal of Colloid and Interface Science 342 (2010) 103-109.
Versteeg et al. Chemosphere 24 (1992) 641-662.

* cited by examiner

*Primary Examiner* — Sun Jae Loewe
(74) *Attorney, Agent, or Firm* — Novak Druce Connolly Bove + Quigg LLP

(57) ABSTRACT

New types of derivatives of tris(2-hydroxyphenyl)methanes which have, as functional groups, polyalkoxy groups or polyalkoxy groups modified with terminal hydrophilic groups, preparation of such compounds and their use, especially as surfactants and thickeners.

18 Claims, 6 Drawing Sheets

DERIVATIVES OF TRIS(2-HYDROXYPHENYL)METHANE, THEIR PREPARATION AND USE

CROSS-REFERENCE TO RELATED APPLICATIONS

This application claims the benefit of U.S. Provisional Application Ser. No. 61/346,482 filed May 20, 2010, the entire contents of which are incorporated herein by reference in its entirety.

FIELD OF THE INVENTION

The present invention relates to new types of derivatives of tris(2-hydroxyphenyl)-methanes which have, as functional groups, polyalkoxy groups or polyalkoxy groups modified with terminal hydrophilic groups. It also relates to the preparation of such compounds and to their use, especially as surfactants and thickeners.

BACKGROUND

Tris(2-hydroxyphenyl)methanes and various derivatives thereof are known in principle.

G. Casiraghi, G. Casnati and M. Cornia, Tetrahedron Letters, No. 9, 679-682 (1973) describe the synthesis of mono- or dialkylated tris(2-hydroxyphenyl)methanes by reacting corresponding phenols with triethyl orthoformates.

M. B. Dinger and M. J. Scott describe in Chem. Commun., 1999, 2525/2526, Inorg. Chem. 2000, 39, 1238-1254 and Inorg. Chem. 2001, 40, 1029-1036 the synthesis of various tris(3,5-dialkyl-2-hydroxyphenyl)methanes, where methyl, t-butyl and t-pentyl radicals are described as alkyl radicals. The trishydroxy compounds are used as complexing agents for zinc and alkali metal ions.

M. B. Dinger and M. J. Scott, Eur J. Org. Chem. 2000, 2467-2478 furthermore describe the further reaction of the OH group of tris(3,5-dialkyl-2-hydroxyphenyl)-methanes. The OH functions can be derivatized through reaction with halogencarboxylic acid esters and hydrolysis and/or further reactions. Dinger and Scott describe, for example, tris(3,5-di-t-butyl-2-carboxymethoxyphenyl)methane, tris(3,5-di-tert-butyl-2-[(dimethylamido)methoxy]phenyl)methane, tris{3,5-di-tert-butyl-2-[N-(methylglycyl)carbonylmethoxy]phenyl}methane and tris(3,5-di-tert-butyl-2-[(benzylaminocarbonyl)methoxy]phenyl)methane. The derivatives can be used in each case as complexing agent, for example for Zn(II) ions.

K. Matloka, A. Gelis, M. Regalbuto, G. Vandegift and M. J. Scott, Dalton Trans., 2005, 3719-3721 or Separation Science and Technology, 41, 2006, 2129-2146 and M. W. Peters, E. J. Werner and M. J. Scott, Inorg. Chem., 2002, 41, 1701-1716 disclose functionalized tris(3,5-dialkyl-2-hydroxyphenyl) methanes, and specifically tripodal diglycolamides and their use for the complexing and separation of lanthanides. Tris(3, 5-dialkyl-2-hydroxyphenyl)methanes in which the OH group is etherified with ω-amino or cyanoalkyl groups are used as intermediate of the synthesis.

R. Mitra, M. W. Peters and M. Scott, Dalton Trans., 2007, 3924-3935, further describe tris(2-hydroxyphenyl)methane derivatives which have terminal 2-pyridylmethyl-piperazine groups. These molecules can bind zinc ions and are used as catalysts for the phosphate diester synthesis. Tris[2-(2-hydroxyethoxy)-3-methyl-5-t-butylphenyl]-methane is disclosed as intermediate of the multistage synthesis.

EP 597 806 A1 discloses cyclohexyl group-containing glydidyl ethers for use as reactive thinners, flexibilizers or adhesion improvers. Various tris(2-hydroxyphenyl)methanes are described as intermediate of the synthesis, including those in which the OH function is etherified with a (substituted) 2-hydroxyethyl group.

US 2009/0155714 A1 discloses compositions for producing photoresists. Various tris(2-hydroxyphenyl)methane derivatives in which the OH function is esterified in each case with various carboxylic acids are used as a component for this.

It is known that surfactants aggregate to give micelles above the critical micelle concentration (cmc). The shape of these water-soluble aggregates depends on the structure of the surfactants and also on external parameters such as temperature or electrolyte concentration. Typically, spherical or rod-shaped micelles can form above the micelle concentration.

Under certain structural conditions and/or external parameters, long thread-like or worm-like micelles or associates can also form. Even at a relatively low surfactant concentration, this can lead to looping and overlapping of these long aggregates, as a result of which the viscosity of the surfactant solution increases significantly. A certain minimum stability of the micelles over time is prerequisite here. This temporarily formed network of surfactant micelles reacts, from a rheological point of view, either viscously or elastically, for which reason the term viscoelastic surfactant solutions is generally used. Micelles liberate individual surfactants, incorporate surfactants into the micelle association, disintegrate and reform again. Surfactant micelles which form viscoelastic networks are very stable over time before they disintegrate into individual segments and reform again, meaning that the micellar network can offer resistance to shearing of the surfactant solution and thereby reacts either viscously or else elastically. Further details relating to viscoelastic surfactants forming worm-like micelles such as hexadecyltrimethylammonium p-toluenesulfonate or cetylpyridinium salicylate are described, for example, in H. Hoffmann et al., Adv. Colloid Interface Sci. 1982, 17, 275-298 or M. R. Rojas et al., Journal of Colloid and Interface Science 342 (2010) 103-109).

On account of the properties discussed, viscoelastic surfactants are very particularly suitable as thickeners and can be used in various areas of technology.

US 2005/0155762 discloses betaines with alkyl chains having 14 to 24 carbon atoms, for example oleylamidopropylbetaine or erucylamidopropylbetaine as viscoelastic surfactants with a thickening effect.

U.S. Pat. No. 7,461,694 B2 discloses zwitterionic surfactants with alkyl chains of from 16 to 24 carbon atoms as viscoelastic surfactants.

WO 2008/100436 A1 discloses a viscoelastic surfactant mixture of cationic, anionic or zwitterionic surfactants and a polymer. The surfactants have alkyl chain lengths of from 12 to 25 carbon atoms.

In the cited disclosures, surfactants with long alkyl chains are used in each case for the formation of viscoelastic surfactant solutions. One disadvantage of viscoelastic surfactants with long alkyl chains is that, upon contact with nonpolar liquids, they solubilize these, as a result of which the worm-like micelles are converted to spherical aggregates and the viscoelasticity is lost. Moreover, in contact with other surfactants, these viscoelastic surfactants generally form mixed micelles, as a result of which the viscoelasticity can likewise be lost. Structures with short alkyl chains or structures which deviate from the customary linear structure principle of the surfactants as a rule form spherical micelles or only short anisometric aggregates and thus no viscoelastic surfactant solutions.

The best known viscoelastic surfactants are cationic surfactants such as hexadecyltrimethylammonium p-toluenesulfonate or cetylpyridinium salicylate. Cationic surfactants with long alkyl radicals are ecotoxicologically very acceptable (see e.g. Versteeg et al. Chemosphere 24 (1992) 641)). Since they adsorb particularly well on surfaces on account of their positive charge, they moreover lose some of their effect in the case of some applications. There is therefore a need for surfactants with a more favorable ecotoxicological profile and lower adsorption tendency.

BRIEF SUMMARY

It was an object of the invention to find new types of compounds which should be suitable in particular for the formation of viscoelastic surfactant solutions.

Surprisingly, it has been found that as the result of a suitable derivatization of tris(2-hydroxyphenyl)methane, new types of compound with a new type of properties profile can be obtained. In particular, it is possible to obtain surfactants which are suitable for the preparation of viscoelastic surfactant solutions.

Accordingly, derivatives of tris(2-hydroxyphenyl)methane have been found, where the tris(2-hydroxyphenyl)methane derivatives have the general formula (I)

where the radicals $R^1$, $R^2$ and R have the following meaning:

R: independently of one another, 0 to 4 $C_1$- to $C_{30}$-hydrocarbon radicals per phenyl ring, $R^1$: a radical selected from the group of H, OH, F, Cl, Br, I and $C_1$- to $C_{30}$-hydrocarbon groups, $R^2$: independently of one another, radicals of the general formula —($R^5$—O—)$_n$—$R^6$—X (III), where n is a number from 1 to 50, and where the radicals $R^5$, independently of one another, are selected from the group of radicals $R^7$, $R^8$ and $R^9$ where $R^6$, X, $R^{10}$ and $R^{11}$, independently of one another, have the following meaning:

$R^6$: a single bond or an alkylene group having 1 to 10 carbon atoms which can have optionally functional groups as substituents, X: H or a hydrophilic group, $R^{10}$: H or a $C_1$- to $C_6$-hydrocarbon radical, $R^{11}$: a group —($R^5$—O—)$_m$—$R^6$—X, where m is a number from 0 to 50, and where the total number z of all groups $R^5$ in a radical $R^2$ is 1 to 50, with the proviso that z is a number from 2 to 50, if at least one X is H.

Furthermore, the preparation of such compounds and their use, in particular as surfactants and thickeners, has been found.

DETAILED DESCRIPTION OF THE PREFERRED EMBODIMENTS

As regards the invention, the following may be stated specifically:

Compounds According to the Invention

The compounds according to the invention are derivatives of tris(2-hydroxyphenyl)methane of the general formula (I).

(I)

The radical $R^1$ is a radical selected from the group of H, OH, F, Cl, Br, I, or straight-chain, branched or cyclic, aliphatic and/or aromatic $C_1$- to $C_{30}$-hydrocarbon groups. It is preferably H, Cl, a straight-chain or branched $C_1$- to $C_{12}$-alkyl group or a benzyl group. $R^1$ is particularly preferably H.

The three phenyl rings can in each case be substituted in the 3, 4, 5 and 6 position, independently of one another, with hydrocarbon radicals R having 1 to 30 carbon atoms, where the groups can be arranged as desired. Preferably, there is 1 or 2 groups R per phenyl ring. The groups R may be straight-chain, branched or cyclic, aliphatic and/or aromatic hydrocarbon radicals. Preferably, they are preferably straight-chain, branched or cyclic aliphatic hydrocarbon groups having 1 to 20, particularly preferably 1 to 12 carbon atoms. Examples of suitable groups R comprise methyl, ethyl, n-propyl, isopropyl, n-butyl, i-propyl, t-butyl, n-pentyl, 1,1-dimethylpropyl, 2,2-dimethylpropyl, 3-methylbutyl, hexyl, 2-ethylhexyl, heptyl, octyl, nonyl, decyl, undecyl, dodecyl, cyclopentyl, cyclohexyl, adamantyl or benzyl groups.

Preferably, the compounds according to the invention have the general formula (II).

(II)

In formula (II), $R^3$ and $R^4$, in each case independently of one another, are H or hydrocarbon radicals having 1 to 30 carbon atoms, preferably 1 to 20 carbon atoms, particularly preferably 1 to 12 carbon atoms. The hydrocarbon radicals can be straight-chain, branched, cyclic, aliphatic and/or aromatic. They are preferably straight-chain, branched or cyclic aliphatic hydrocarbon groups having 1 to 20, particularly preferably 1 to 12, carbon atoms and very particularly preferably straight-chain or branched aliphatic hydrocarbon radicals having 1 to 6 carbon atoms.

Examples of suitable hydrocarbon groups comprise methyl, ethyl, propyl, isopropyl, n-butyl, isobutyl, t-butyl, n-pentyl, 1,1-dimethylpropyl, 2,2-dimethylpropyl, 3-methylbutyl, hexyl, 2-ethylhexyl, heptyl, octyl, nonyl, decyl, undecyl, dodecyl, cyclopentyl, cyclohexyl or adamantyl groups.

Preferably, $R^3$ and $R^4$ are H or methyl, ethyl, propyl, isopropyl, n-butyl, isobutyl, t-butyl, n-pentyl, 1,1-dimethylpropyl, 2,2-dimethylpropyl, 3-methylbutyl groups, 1,1,3,3-tetramethylbutyl, particularly preferably t-butyl groups.

In one preferred embodiment of the invention, at least one of the radicals $R^3$ or $R^4$ is not H; in this embodiment, the radical $R^3$ is particularly preferably not H. Very particularly preferably, both radicals $R^3$ and $R^4$ are in each case not H. Preferred, particularly preferred and very particularly preferred combinations of radicals $R^3$ and $R^4$ are given in Tables 1, 2 and 3 below:

TABLE 1

List of preferred combinations

| $R^3$ | $R^4$ |
|---|---|
| t-Butyl | H |
| t-Butyl | Methyl |
| t-Butyl | Ethyl |
| t-Butyl | t-Butyl |
| Me | Me |
| Me | tBu |
| 1,1-Dimethylpropyl | H |
| 1,1-Dimethylpropyl | Methyl |
| 1,1-Dimethylpropyl | Ethyl |
| 1,1-Dimethylpropyl | t-Butyl |
| 1,1-Dimethylpropyl | 1,1-Dimethylpropyl |
| 1,1,3,3-Tetramethylbutyl | 1,1,3,3-Tetramethylbutyl |
| t-Butyl | 1,1,3,3-Tetramethylbutyl |

TABLE 2

List of particularly preferred combinations

| $R^3$ | $R^4$ |
|---|---|
| t-Butyl | Methyl |
| t-Butyl | t-Butyl |
| 1,1-Dimethylpropyl | Methyl |
| 1,1-Dimethylpropyl | 1,1-Dimethylpropyl |
| 1,1,3,3-Tetramethylbutyl | 1,1,3,3-Tetramethylbutyl |
| t-Butyl | 1,1,3,3-Tetramethylbutyl |

TABLE 3

List of very particularly preferred combinations

| $R^3$ | $R^4$ |
|---|---|
| t-Butyl | t-Butyl |
| 1,1-Dimethylpropyl | 1,1-Dimethylpropyl |
| 1,1,3,3-Tetramethylbutyl | 1,1,3,3-Tetramethylbutyl |
| t-Butyl | 1,1,3,3-Tetramethylbutyl |

Very particularly preferably, both $R^3$ and $R^4$ are t-butyl radicals.

The radicals $R^2$ in the aforementioned formulae (I) and (II) are, independently of one another, radicals of the general formula —$(R^5$—O—$)_n$—$R^8$—X (III).

The radicals $R^5$ in formula (III) are, independently of one another, groups selected from the group of radicals $R^7$, $R^8$ and $R^9$ Here, in the groups $R^7$, the radicals $R^{10}$, independently of one another, are H or a hydrocarbon radical having 1 to 6 carbon atoms, preferably an aliphatic hydrocarbon radical having 1 to 6 carbon atoms. Instead of the orientation —$CH_2$—$CH(R^{10})$— shown in formula (III), the alkylene group can also be incorporated into the polyoxyalkylene chain in inverse orientation —$CH(R^{10})$—$CH_2$—. Formula (III) is intended to comprise both orientations, it also of course being possible for both orientations to be present in one chain. Examples of radicals $R^{10}$ comprise H and also methyl, ethyl, n-propyl or phenyl radicals. In particular, $R^{10}$ is H, methyl, ethyl or n-propyl radicals, preferably H, methyl or ethyl radicals, particularly preferably H or methyl.

In the groups $R^8$ and $R^9$, the groups $R^{11}$ are groups of the general formula —$(R^5$—$O$—$)_m$—$R^6$—$X$, where m is a number from 0 to 50. It may thus (for the case m=0) be a group —$R^6$—$X$, which is linked directly to the O atom, or (for the case m>0) a group in which —$R^6$—$X$ is linked to the O atom via a polyalkoxy group. On account of the fact that in the latter case $R^{11}$ itself can again comprise groups $R^8$ and $R^9$, the groups $R^2$ can also be branched several times.

The radicals $R^7$, $R^8$ and $R^9$ can be arranged as desired in the radicals $R^2$, for example randomly, blockwise, alternately or with a gradient.

In the above radicals, X is in each case H or a hydrophilic group. Preferably, a hydrophilic group comprises one or more oxygen atoms. Depending on the type of the radical $R^2$, only one group X or else two or more groups X may be present in a radical $R^2$. Hydrophilic groups may in particular be acidic groups, preferably a group selected from the group of carboxyl groups —COOM, sulfonic acid groups —$SO_3M$, sulfate groups —$OSO_3M$, phosphonic acid groups —$PO_2M_2$ or phosphoric acid groups —$OPO_3M_2$, where M is $H^+$ or a k-valent counterion $1/kY^{k+}$. The acidic groups can thus be present as free acid and/or as a salt thereof. If M is not $H^+$, it is preferably a monovalent counterion, such as, for example, $NH_4^+$—, ammonium ions with organic radicals or alkali metal ions. Preferred acidic groups are those selected from the group of carboxyl groups —COOM, sulfonic acid groups —$SO_3M$ or sulfate groups —$OSO_3M$, particularly preferably sulfate groups —$OSO_3M$.

Preferred hydrophilic groups further comprise radicals which comprise at least one, preferably at least 2, OH groups, in particular mono- or oligosaccharide radicals, preferably monosaccharide radicals. These may in principle be all types of saccharides. Preferably, radicals derived from pentoses and hexoses, in particular from hexoses, can be used. Examples of suitable monosaccharides comprise glucose, mannose, galactose, fructose or ribose. Preferably, radicals derived from glucose can be used. These may also be derivatives of the saccharides, for example products arising from the saccharides as a result of reduction or oxidation. In particular, derivatives of this type may be sugar acids, such as, for example, gluconic acid.

Examples of other hydrophilic groups comprise, for example, amine oxide groups.

$R^6$ is a single bond or an alkylene group having 1 to 10 carbon atoms, preferably 1 to 3 carbon atoms, which can optionally have functional groups as substituents, in particular an OH group. Examples of such groups comprise —$CH_2$—, —$CH_2CH_2$—, —$CH_2$—$CH_2$—$CH_2$— or —$CH_2$—$CH(OH)$—$CH_2$— groups.

The total number of all groups $R^5$ in a radical $R^2$, i.e. the groups $R^5$ in the main group and also the groups $R^5$ in any branches present, will be referred to hereinbelow as z. If it is a linear group $R^2$, z corresponds to the number n.

According to the invention, z is a number from 2 to 50 if at least one X is H, and it is a number from 1 to 50 if no X is H. The numbers z, n and m refer here in a known manner to the average value of the alkoxy groups present in the molecule, where the average value of course does not have to be a natural number, but may also be a positive rational number. As a rule, irrespective of the nature of the substituent X, z is a number from 2 to 50, in particular 4 to 40, preferably 5 to 30, particularly preferably 8 to 20 and very particularly preferably 10 to 15.

From the possible groups (III) and the radicals $R^1$, $R^2$, $R^3$ and $R^4$, the person skilled in the art makes an appropriate selection depending on the desired intended use of the compounds.

In one first preferred embodiment of the invention, at least one of the radicals $R^5$ is a radical $R^7$. In one particularly preferred embodiment of the invention, all of the radicals $R^5$ are radicals $R^7$. If the radicals $R^7$ comprise different radicals $R^{10}$, these may be arranged in any desired manner, for example randomly, blockwise, alternately or with a gradient. Preferably, at least some of the z radicals $R^{10}$ are H, in particular at least 20%, preferably at least 50%, particularly preferably at least 80% and very particularly preferably all radicals $R^{10}$ are H.

In a second preferred embodiment of the invention, the radicals $R^2$ are groups —$(R^7$—$O$—$)_n$—$R^6$—$X$ (IIIa). Radicals $R^8$ and radicals $R^9$ are not present in this embodiment. Particularly preferably these are groups —$(R^7$—$O$—$)_n$—$H$ (IIIb), i.e. $X=H$ and $R^6$ is a single bond. In (IIIa) and (IIIb), n is a number 5 to 30, particularly preferably 8 to 20 and very particularly preferably 10 to 15. The radicals $R^{10}$ in the radicals $R^7$, i.e. the radicals —$CH_2$—$CH(R^{10})$—, are, independently of one another, a radical selected from the group of H, methyl or ethyl, where at least 50% of the radicals ($R^{10}$) are H, preferably at least 80% of the radicals and very particularly preferably all of the radicals $R^{10}$ are H. If two or more different radicals $R^{10}$ are present, these can be arranged randomly, alternately or blockwise. In the case of a blockwise arrangement, it is preferred if the ethylene oxide groups (i.e. $R^{10}=H$) form the terminal block.

In a third preferred embodiment of the invention, the radicals $R^2$ are groups —(—$CH_2$—$CH(R^{12})$—$O$—$)_a$—(—$CH_2$—$CH_2$—$O$—$)_b$—$H$ (IIIc), where the two blocks are arranged in this order. It is thus again an embodiment in which only groups $R^7$ are present, X is H and $R^6$ is a single bond. The radicals $R^{12}$ in the formula (IIIc) are hydrocarbon radicals having 1 to 6 carbon atoms, preferably aliphatic hydrocarbon radicals having 1 to 6 carbon atoms, preferably a methyl and/or an ethyl group. a is numbers from 1 to 49, preferably 1 to 10, and b is numbers from 1 to 49, preferably 1 to 20, with the proviso that a+b=n=2 to 50. Preferably, b is $\geq a$.

In a fourth preferred embodiment of the invention, the radicals $R^2$ are groups —(—$CH_2$—$CH(R^{13})$—O—)$_n$—$R^6$—X (IIId), where in at least one of the groups $R^2$, the radical X is not H. The radicals $R^{10}$ in the formula (IIId) are, independently of one another, a radical selected from the group of H, methyl or ethyl, where at least 20% of the radicals $R^{10}$ are H, preferably at least 50% of the radicals, particularly preferably at least 80% of the radicals and particularly preferably all of the radicals $R^{10}$ are H. If two or more different radicals $R^{13}$ are present, these can be arranged randomly, alternately or blockwise. In the case of a blockwise arrangement, it is preferred if the ethylene oxide groups (thus $R^{13}$=H) form the terminal block. Preferably, X in formula (IIIc) is carboxyl groups —COOM, sulfonic acid groups —$SO_3M$, sulfate groups —$OSO_3M$. For example, it may be groups —(—$CH_2$—$CH(R^{13})$—O—)$_n$—H in combination with groups —(—$CH_2$—$CH(R^{13})$—O—)$_n$—$SO_3H$. In this embodiment, n is preferably numbers from n=1 to 30.

In a fifth preferred embodiment of the invention, the radicals $R^2$ of the general formula —($R^5$—O—)$_n$—$R^6$—X (III) comprise radicals $R^8$ and/or $R^9$. These may either be radicals which exclusively comprise groups $R^8$ and/or $R^9$, or those which, besides $R^8$ and/or $R^9$, additionally comprise groups $R^7$. Preferably, $R^7$ is groups $R^7$ where $R^{10}$=H, i.e. groups derived from ethylene oxide.

In a sixth preferred embodiment of the invention, $R^2$ is radicals of the general formula —(—$CH_2CH(CH_2OH)$—O—)$_c$($CH_2CH(R^{14})$—O—)$_d$—$R^6$—X (IIIe), where the sum of c+d=z. In the formula (IIIe), these are monomers $R^7$ and $R^8$, where $R^{11}$ is H. The radicals $R^{14}$ in the formula (IIIe) are, independently of one another, a radical selected from the group of H, methyl or ethyl, where at least 20% of the radicals $R^{10}$ are H, preferably at least 50% of the radicals, particularly preferably at least 80% of the radicals and particularly preferably all of the radicals $R^{14}$ are H. In this embodiment, $R^6$ is preferably a single bond and X is preferably H.

In a further embodiment of the invention, they are derivatives of tris(2-hydroxyphenyl)methanes which are obtainable by free-radically polymerizing carboxylic acid vinyl esters in the presence of compounds of the general formulae (I) or (II). The polymerization of carboxylic acid vinyl esters in the presence of polyalkoxy groups is known in principle to the person skilled in the art. In this reaction, vinyl ester, oligovinyl ester and/or polyvinyl ester groups graft onto the polyalkoxy groups, i.e. additional polyalkoxy groups having side groups are formed. The polyvinyl ester groups are then at least partially hydrolyzed to OH groups. The OH groups can then optionally be functionalized with groups —$R^6$—X. The reaction scheme is illustrated below by way of example.

Suitable carboxylic acid vinyl esters comprise in particular vinyl formate, vinyl acetate and vinyl propionate. Of particular suitability for the modification are in particular compounds which have groups (IIIb) or (IIIc).

Preparation of the Compounds According to the Invention

To prepare the compounds according to the invention, firstly tris(2-hydroxyphenyl)methane compounds of the general formulae (IV) or (V) having the desired substitution pattern as regards $R^1$ and R or $R^3$ and $R^4$ can be synthesized.

The methods for the preparation of the compounds are described in detail in the literature cited at the start, for example G. Casiraghi, G. Casnati and M. Cornia, Tetrahedron Letters, No. 9, 679-682 (1973), M. B. Dinger and M. J. Scott, Chem. Commun., 1999, 2525/2526, Inorg. Chem. 2000, 39, 1238-1254, and Inorg. Chem. 2001, 40, 1029-1036,

M. B. Dinger and M. J. Scott, Eur J. Org. Chem. 2000, 2467-2478, K. Matloka, A. Gelis, M. Regalbuto, G. Vandegift and M. J. Scott, Dalton Trans., 2005, 3719-3721, M. W. Peters, E. J. Werner and M. J. Scott, Inorg. Chem., 2002, 41, 1701-1716 and R. Mitra, M. W. Peters and M. Scott, Dalton Trans., 2007, 3924-3935.

The tris(2-hydroxyphenyl)methane compounds of the general formulae (IV) or (V) can be alkoxylated in a second step in a manner known in principle.

Carrying out alkoxylations is known in principle to the person skilled in the art. It is likewise known to the person skilled in the art that the molecular weight distribution of the alkoxylates can be influenced by the reaction conditions, in particular the choice of catalyst.

$C_2$- to $C_8$-Alkylene oxides are used for the alkoxylation, for example ethylene oxide, propylene oxide, butylene oxide or styrene oxide. In each case, preference is given to the 1,2-alkylene oxides. The use of these alkylene oxides leads to groups which comprise radicals $R^7$.

In order to obtain radicals $R^8$ and $R^9$, glycidol (VIa) or glycidol (VIb) protected with a suitable protective group $R^{15}$ (VIa)

(VIb)

is used as alkene oxide. $R^{15}$ can in principle be all types of groups with which the OH function can be protected during the alkoxylation. They can be cleaved off after the alkoxylation or only following introduction of the groups —$R^6$—X in a manner known in principle. $R^{15}$ may be, for example, a t-butyl group or a benzyl group.

Since, after the reaction of the unprotected glycidol, two OH groups are present in the chain which can further react, the branches already cited are formed in the radical $R^2$. Using the protected glycidol, it is possible to introduce groups $R^8$ of the formula —$CH_2$—$CH(CH_2OH)$— into the radical $R^2$ in a targeted manner.

The alkoxylation may be a base-catalyzed alkoxylation. For this, the tris(2-hydroxyphenyl)methane compounds can be admixed in a pressurized reactor with alkali metal hydroxides, preferably potassium hydroxide, or with alkali metal alcoholates, such as, for example, sodium methylate. As the result of reduced pressure (for example <100 mbar) and/or increasing the temperature (30 to 150° C.), water still present in the mixture can be drawn off. The alcohol is then present as the corresponding alcoholate. The system is rendered inert with inert gas (e.g. nitrogen) and the alkylene oxide(s) is/are added stepwise at temperatures of from 60 to 180° C. up to a pressure of max. 10 bar. At the end of the reaction, the catalyst can be neutralized by adding acid (e.g. acetic acid or phosphoric acid) and, if required, can be filtered off. Optionally, the alkoxylation can also be carried out in the presence of a solvent. This can be e.g. toluene, xylene, dimethylformamide or ethylene carbonate.

The alkoxylation of the alcohols can, however, also be undertaken by means of other methods, for example by acid-catalyzed alkoxylation. Furthermore, double hydroxide clays as described in DE 43 25 237 A1, for example, can be used, or it is possible to use double metal cyanide catalysts (DMC catalysts). Suitable DMC catalysts are disclosed, for example, in DE 102 43 361 A1, in particular sections [0029] to [0041], and the literature cited therein. For example, catalysts of the Zn—Co type can be used. To carry out the reaction, the alcohol R—OH can be admixed with the catalyst, and the mixture can be dewatered as described above and be reacted with the alkylene oxides as described. Usually, not more than 1000 ppm of catalyst as regards the mixture are used, and, on account of this small amount, the catalyst can remain in the product. The amount of catalyst can as a rule be less than 1000 ppm, for example 250 ppm and less.

The alkoxylation can alternatively also be undertaken by reaction of the compounds (IV) and (V) with cyclic carbonates, such as, for example, ethylene carbonate.

By means of the alkoxylation, compounds according to the invention are already obtained, namely those where X═H. These have terminal OH groups. This is shown in FIGS. (VII) and (VIII) below by way of example using compounds according to the invention which have polyalkoxy chains from groups $R^7$.

(VII)

(VIII)

To introduce groups X which are not H, the alkoxylated tris(2-hydroxyphenyl)methane derivatives having terminal OH groups and of the formula (VII) or (VIII) are further functionalized with groups —$R^6$—X in a suitable manner. This gives compounds of the general formula (IX) or (X).

(IX)

-continued (X)

Derivatives comprising sulfate groups —OSO$_3$M can be obtained by reacting the terminal OH groups with SO$_3$, sulfuric acid, chlorosulfuric acid or aminosulfonic acid (CAS No. 5329-14-6) and subsequently neutralizing with e.g. sodium hydroxide solution. This can be carried out e.g. in a falling-film reactor. As a result of this reaction, only the terminal OH groups are substituted by sulfate groups. In this reaction, R$^6$ is a double bond.

Derivatives comprising sulfonate groups —SO$_3$M can be obtained by substituting the OH group for Cl using phosgene or thionyl chloride. The reaction can be undertaken in the presence of a solvent such as e.g. chlorobenzene. Here, HCl that is released and also CO$_2$ or SO$_2$ that is released can advantageously be removed from the system by stripping with nitrogen, such that ether cleavage is suppressed. The alkylalkoxychlorine compound is then reacted with an aqueous solution of sodium sulfite, where the chloride is substituted by sulfite and the sulfonate is obtained. The substitution can be undertaken in the presence of a phase mediator (for example C$_1$- to C$_8$-alcohols) at a temperature 100-180° C. and under pressure. The sulfonates can alternatively be obtained by adding vinylsulfonic acid onto the compound (V). Details on this are described for example in EP 311 961 A1. Sulfonates can furthermore be obtained by reacting the compounds (V) with 1,3-propanesultone or 1,4-butanesultone. Here, sulfonates with a terminal group —CH$_2$—CH$_2$—CH$_2$—SO$_3$M (i.e. R$^6$=—CH$_2$—CH$_2$—CH$_2$—) or —CH$_2$—CH$_2$—CH$_2$—CH$_2$—SO$_3$M (i.e. R$^6$=—CH$_2$—CH$_2$—CH$_2$—CH$_2$—) are obtained. Compounds with a terminal group —CH$_2$—CH(OH)—CH$_2$—SO$_3$M (i.e. R$^6$=—CH$_2$—CH(OH)—CH$_2$—) can be obtained by reaction of the compound (V) with epichlorohydrin and subsequent nucleophilic substitution of the chloride group by sodium sulfite.

Derivatives comprising carboxylate groups —COOM can be obtained by oxidation of the compound (V). Of suitability for this are all oxidizing agents, if appropriate in conjunction with suitable catalysts which are able to oxidize the terminal OH group of the compound (V) to the COOH group, without oxidizing other parts of the molecule to a large extent. The oxidation can be undertaken, for example, with the help of air or oxygen using a precious-metal catalyst (for example a catalyst based on palladium). In the case of this synthesis variant, a terminal group —CH$_2$—COOM is obtained (i.e. R$^6$=—CH$_2$—). Carboxylates can furthermore also be prepared by adding (meth)acrylic acid or a (meth)acrylic acid ester onto the OH groups by means of a Michael addition. If the esters are used, these are saponified after the addition. In the case of this synthesis variant, terminal groups —CH$_2$—CH$_2$—COOM or —CH$_2$—CH(CH$_3$)—COOM are obtained depending on whether acrylic acid or (meth)acrylic acid or esters thereof have been used.

Phosphate groups can be introduced by reacting with phosphorus pentoxide, phosphonate groups by reacting with vinylphosphonic acid.

Compounds with mono- or oligosaccharide groups can be prepared by converting the corresponding saccharide, for example glucose, into the corresponding butyl acetal with the help of an acidic catalyst, such as, for example, para-toluenesulfonic acid and n-butanol. The resulting water of reaction can be removed from the reaction mixture by applying a vacuum. The compound (V) is then added and the transacetalation is driven forward as a result of the distillative removal of the butanol from the equilibrium. The acidic catalyst can be neutralized at the end of the reaction by adding base, for example NaOH or KOH.

Depending on the type of groups R$^2$, the resulting compounds have only one terminal group —R$^6$—X or else two or more terminal and/or pendant groups —R$^6$—X.

When introducing the terminal group —R$^6$—X, it is of course not necessary for all of the OH groups in the H-terminated compounds according to the invention to be reacted. It is possible to react only some of the groups, for example only, on average, every third group. In this way, it is possible to adapt the properties of the compounds according to the invention to the desired intended use.

When using glycidol, various synthesis variants are conceivable. If unprotected glycidol is used, then the groups R$^2$ can be branched and have two or more terminal or pendant OH groups. These groups can be converted in their entirety or else only partly to the groups —R$^6$—X. In the case of an only partial conversion, the conversion takes place randomly.

If protected glycidol (VIb) is used, then firstly an unbranched polyalkoxy chain with a terminal OH group and pendant, protected OH groups is formed. It is then possible on the one hand to firstly cleave off the protective groups and then to undertake the introduction of the groups —R$^6$—X. In this case, a linear group R$^2$ which has terminal and/or pendant groups —R$^6$—X is formed. If, in an alternative synthesis, the protective groups are not firstly cleaved off, but the introduction of the groups —R$^6$—X is firstly undertaken, then only the terminal OH groups react. The elimination of the protective groups can then take place. In this case, a group R$^2$ is formed which has a terminal group —R$^6$—X and, moreover, pendant methylol groups —CH$_2$OH.

Use of the Compounds According to the Invention

The novel compounds are suitable for use as surfactants. They are suitable in particular for the preparation of viscoelastic surfactant solutions and can therefore be used as a component of thickening formulations. Suitable surfactants are in particular compounds of the general formula (II) in which the radicals R$^3$ and R$^4$ are not H, and in which the radicals R$^2$ have the general formulae (IIIb), (IIIc) or (IIId). They lower the surface tension of water to values typical for surfactants of below 35 mN/m and form micelles even at concentrations below 0.1 g/l. The micelles formed are very stable, and consequently the surfactants are not very dynamic.

On account of their interface-active properties, however, the novel compounds are also suitable, due to their thickening effect, furthermore for example for use in detergents and cleaners, paints and coatings, in cosmetic and pharmaceutical formulations, paper, textile and leather auxiliaries, formulations for human and animal nutrition, the construction sector, crop protection formulations, and generally for producing emulsions and dispersions. Compared with nonpolar liquids, these surfactants lower the oil/water interfacial tension to values below 5 mN/m, depending on the type of oil used and the radicals $R^3$ to $R^4$.

Tris(3,5-di-tert-butyl-2-hydroxyphenyl)methane reacted with ethylene oxide, in particular with 9 to 14 EO units per polyalkoxy group, for example, is particularly highly suitable as surfactants.

The examples below are intended to illustrate the invention in more detail:

I) Synthesis of the Compounds According to the Invention

Synthesis Example 1

Synthesis of tris(3,5-di-tert-butyl-2-hydroxyphenyl)methane

Tris(3,5-di-tert-butyl-2-hydroxyphenyl)methane (CAS No. 143560-44-5) was prepared by means of the process described by M. B. Dinger, M. J. Scott, Eur. J. Org. Chem. 2000, 2467. Tris(3,5-di-tert-butyl-2-hydroxyphenyl)methane is hereinbelow also abbreviated as TRIS.

Synthesis Example 2

Synthesis of $TRIS[(-CH_2-CH_2-O)_{11}H]_3$ by ethoxylation of TRIS with 33 EO units In a 2 l autoclave, TRIS (100 g) suspended in toluene (150 ml) is admixed with potassium tert-butylate (3.0 g). Flushing with $N_2$ is carried out three times, a preliminary pressure of ca. 1.3 bar of $N_2$ is established and the temperature is increased to 119-121° C. Ethylene oxide (231 g) is metered in such that the temperature remains between 119° C.-130° C. The mixture is then afterstirred for 16 h at 90° C., flushed with $N_2$ and cooled to 70° C., and the reactor is emptied. The basic crude product is neutralized with the help of standard commercial Mg silicates, which are then filtered off. This gives 263 g of intermediate, which has an OH number of 105.9 mg/g. In a second step, 239 g of the intermediate obtained in this way are admixed in a 2 l autoclave with potassium tert-butylate (1.5 g). The system is flushed three times with $N_2$, a preliminary pressure of ca. 1.3 bar of $N_2$ is established and the temperature is increased to 119-121° C. Ethylene oxide (231 g) is metered in such that the temperature remains between 119° C.-130° C. The mixture is then afterstirred for 16 h at 100° C., flushed with $N_2$ and cooled to 70° C., and the reactor is emptied. The basic crude product is neutralized with the help of standard commercial Mg silicates, which are then filtered off. This gives 307 g of the target compound. OH number: 87.5 mg/g. The TAI-$^1$H-NMR (lit.: J. Loccufier, M. van Bos, E. Schacht, Polymer Bulletin, 1991, 27, 201) of the substance shows an average degree of ethoxylation of 11 ethylene oxide units per phenolic OH group.

Synthesis Example 3

Synthesis of $TRIS[(-CH_2-CH_2-O)_{11}H]_2[(-CH_2-CH_2-O)_{11}-SO_3Na]$ by Sulfation The product $TRIS[(-CH_2-CH_2-O)_{11}H]_3$ synthesized in Example 2 is dissolved in dichloromethane (45 g) and cooled to 5-10° C. Then, chlorosulfonic acid (2.12 g) is added dropwise such that the temperature does not exceed 10° C. The mixture is stirred for 1 h at 10° C., then overnight at room temperature, before the above reaction mixture is added dropwise to an aqueous NaOH solution (50%, 1.98 g) at max. 10° C. The dichloromethane is removed under gentle vacuum on the rotary evaporator at 30-45° C. The product is characterized by $^1$H-NMR and the water content of the solution is determined (ca. 60%).

Synthesis Example 4

Synthesis of $TRIS[(-CH_2-CH_2-O)_{11}-SO_3Y]_3$ ($Y=Na^+$, $NH_4^+$) by Ethoxylation of TRIS with 33 EO Units and Subsequent Complete Sulfation The product from Synthesis Example 2 (30 g), aminosulfonic acid (CAS 5329-14-6; 5.0 g) and catalytic amounts of urea (17 mg) are heated for 7 h at 85° C. After cooling to room temperature, 35 g of water are added and the pH of the solution obtained in this way is adjusted to pH=9 with 50% strength sodium hydroxide solution. The product is characterized by means of $^1$H-NMR and the water content of the solution is determined (ca. 47%).

Synthesis Example 5

Synthesis of $TRIS[(CH_2CH(CH_3)-O)_3-(-CH_2-CH_2-O)_{13}H]_3$ by Propoxylation of TRIS with 9 PO Units and Subsequent Ethoxylation with 39 EO Units In an autoclave, TRIS (27.7 g) is suspended in toluene (49 g) and admixed with potassium tert-butylate (0.92 g). The system is flushed three times with $N_2$, a preliminary pressure of ca. 1.3 bar of $N_2$ is established and the temperature is increased to 135° C. Propylene oxide (15.3 g) is metered in such that the temperature remains at 135° C. The mixture is then afterstirred for 16 h at 135° C., flushed with $N_2$ and cooled to 70° C., and the reactor is emptied. The basic crude product is neutralized with the help of standard commercial Mg silicates, which are then filtered off. This gives 85 g of intermediate. In a second step, 34 g of the intermediate obtained in this way are dissolved in an autoclave in toluene (70 ml) and admixed with potassium tert-butylate (1.0 g). The system is flushed three times with $N_2$, a preliminary pressure of ca. 1.3 bar of $N_2$ is established and the temperature is increased to 130° C. Ethylene oxide (60 g) is metered in such that the temperature remains at 130° C. The mixture is then afterstirred for 16 h at 80° C., flushed with $N_2$ and cooled to 70° C., and the reactor is emptied. The basic crude product is neutralized with the help of standard commercial Mg silicates, which are then filtered off. This gives 73 g of the target compound. OH number: 67.6 mg/g. The product is characterized by means of $^1$H-NMR.

Synthesis Example 6

Alkoxylation of TRIS with 24 Glycidol Units and 9 Ethylene Oxide Units

In an autoclave, TRIS (50 g) is suspended in toluene (100 g) and admixed with potassium tert-butylate (1.7 g) and crown ether [18]crown-6 (4 g). The system is flushed three times with $N_2$, a preliminary pressure of ca. 1.3 bar of $N_2$ is established and the temperature is increased to 120° C. A mixture of glycidol (142 g) and ethylene oxide (31.5 g) is metered in over a period of 8 h such that the temperature remains at 120° C. The mixture is then afterstirred for 16 h at 80° C., flushed with $N_2$ and cooled to 70° C., and the reactor is emptied. The basic crude product is neutralized with the help of standard commercial Mg silicates, which are then filtered off. This gives 200 g of the target product. The product is characterized by means of $^1$H-NMR.

II) Physicochemical Investigations

IIa) Applied Methods:

Rheology:

In oscillatory shear experiments, the rheological properties of a liquid can be determined. The storage modulus G' characterizes the elastic properties of a material, G" the viscous properties.

Interfacial Activity:

By means of Du Nouy ring method (DIN EN 14210), the surface tension of the surfactant in aqueous solution was determined using a tensiometer. The critical micelle concentration (cmc) was determined from the course of the surface tension as a function of the surfactant concentration.

The interfacial tension of an aqueous surfactant solution towards hexadecane as oil phase was determined in accordance with the hanging drop method.

The maximum bubble pressure method gave information relating to the dynamics of the molecule and the stability of the micelles.

Rheological Investigations

Investigation Series 1:

Investigation of TRIS[(—CH$_2$—CH$_2$—O)$_{11}$H]$_3$

Figure 1:
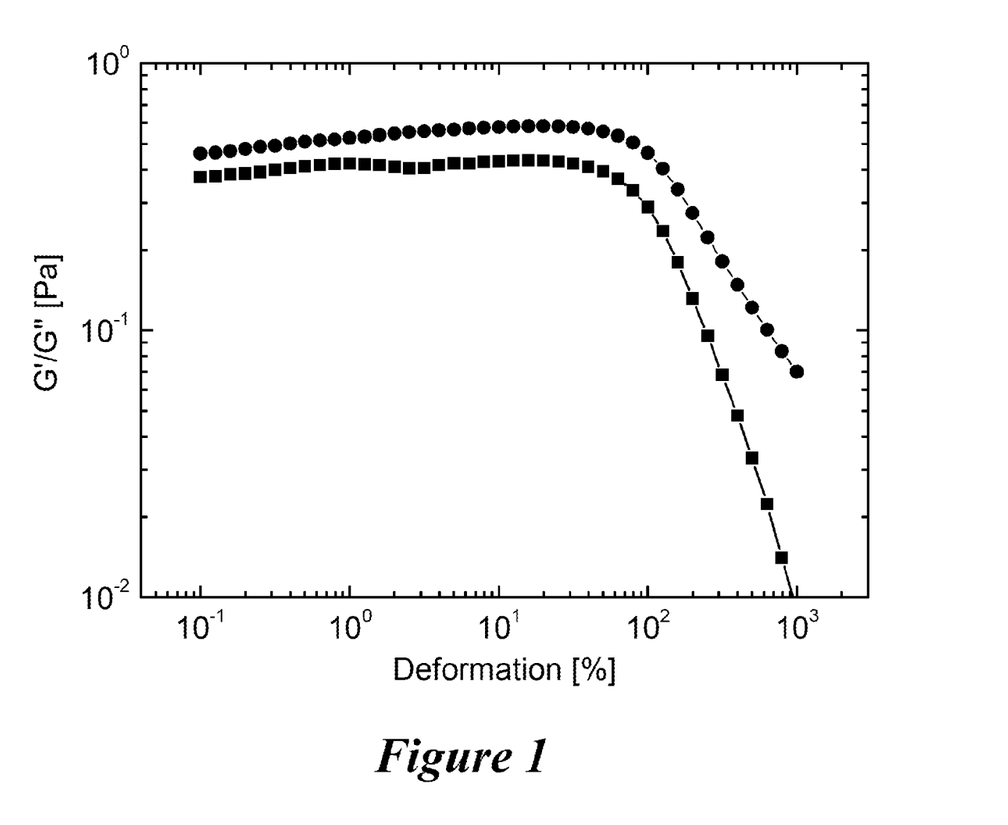
FIG. 1 is a graph showing the storage modulus G' (-■-) and loss modulus G" (-●-) of a 0.9625% strength solution in 185 g/l of saline water of TRIS[(—CH$_2$—CH$_2$—O)$_{11}$H]$_3$ as a function of the deformation at a radian frequency of 10 rad s$^{-1}$.
Figure 2:
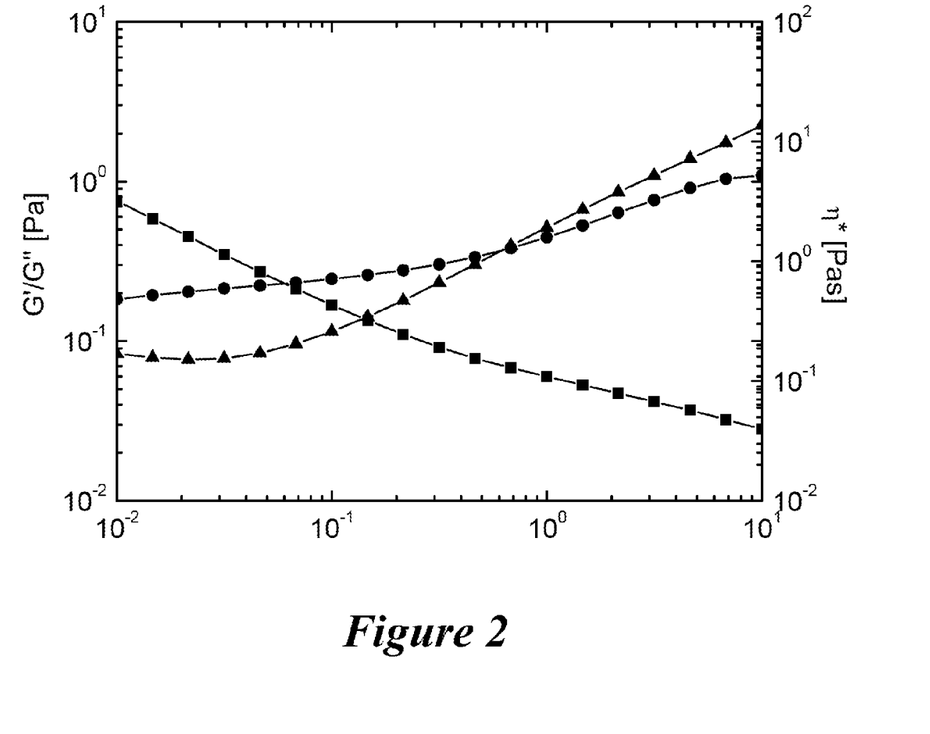
FIG. 2 is a graph showing the storage modulus G' (-●-), loss modulus G" (-▲-) and complex viscosity η* (-■-) of a 0.25% strength solution in 185 g/l of saline water of TRIS [(—CH$_2$—CH$_2$—O)$_{11}$H]$_3$ as a function of the frequency at constant deformation of 10%.

The rheological properties of a 0.25% strength aqueous solution of TRIS[(—CH$_2$—CH$_2$—O)$_{11}$H]$_3$ (as in Synthesis Example 2) were determined at 25° C. The results are summarized in FIGS. 1 and 2. These characterize the viscoelastic properties of the sample (storage modulus and loss modulus) firstly as a function of the deformation and secondly as a function of the frequency of an oscillatory deformation.

Figure 3:
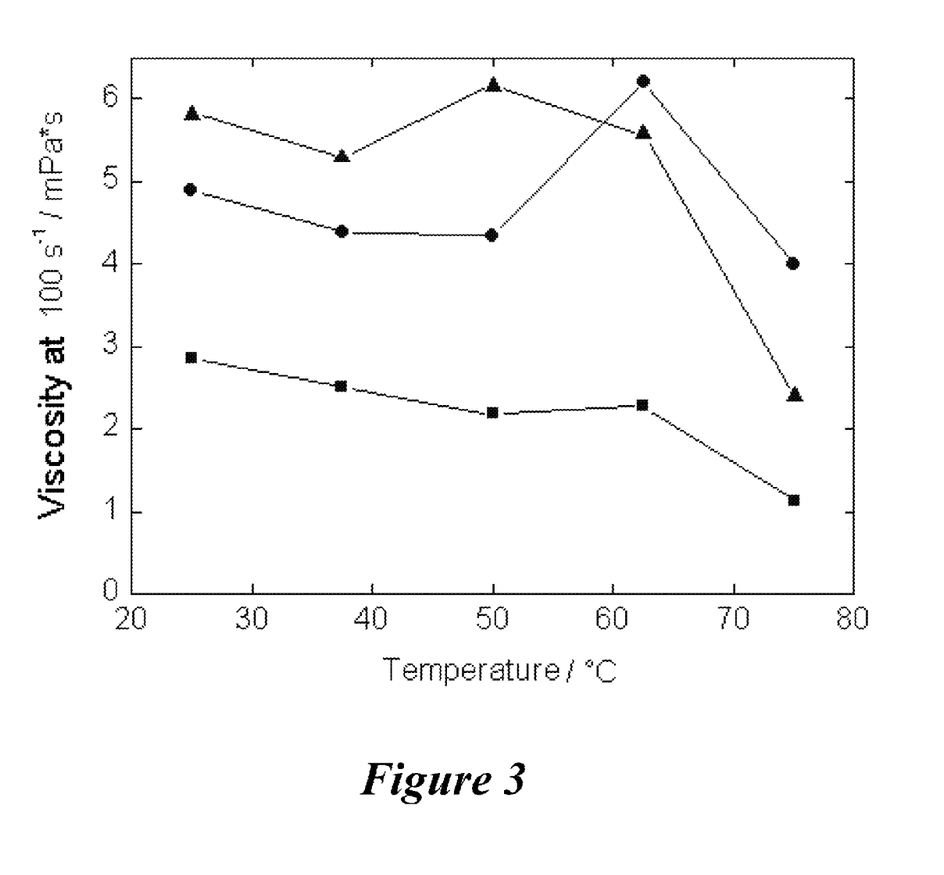
FIG. 3 is a graph showing viscosities as a function of the temperature of a 1% strength solution of TRIS[(—CH$_2$—CH$_2$—O)$_{11}$H]$_3$ in demineralized water (-■-), water with 93 g/l (-●-), and 185 g/l (-▲-) of dissolved salts (shear rate= 100 s$^{-1}$).

Furthermore, the influence of electrolyte concentration and temperature on the viscosity of an aqueous solution of TRIS [(—CH$_2$—CH$_2$—O)$_{11}$H]$_3$ was determined at a constant shear rate of 100 s-1. For this, in each case a 1% solution of TRIS[(—CH$_2$—CH$_2$—O)$_{11}$H]$_3$ in water without the addition of salt, in solution of 93 g/l of NaCl and in solution of 185 g/l of NaCl was investigated at various temperatures. The results are summarized in FIG. 3 and show that the viscosity of the investigated molecule is robust toward salt-containing water and temperature.

Interfacial activity of TRIS[(—CH$_2$—CH$_2$—O)$_{11}$H]$_3$

The surface tension is 32 mN/m (1 g/l, 25° C.).

The critical micelle concentration in completely demineralized water is 0.03 g/l (T=25° C.)

The interfacial tension between completely demineralized water and hexadecane is 4.7 mN/m (c=1 g/l; t=10 min, T=25° C.)

Investigations Relating to the Dynamics:

The measurement of the dynamic surface tension shows that TRIS[(—CH$_2$—CH$_2$—O)$_{11}$H]$_3$ compared to commercial surfactants such as alcohol ethoxylates with alkyl chain lengths between 10 and 15 carbon atoms and degrees of ethoxylation of from 5 to 15 EO is hardly dynamic. This means more precisely that noticeable interfacial activity starts only after 2 seconds, from which it can be concluded that the micelles are very stable. This again is a feature of viscoelastic surfactants.

Investigation Series 2:

Investigation of TRIS[(—CH$_2$—CH$_2$—O)$_{11}$H]$_2$[(—CH$_2$—CH$_2$—O)$_{11}$—SO$_3$Na]

Figure 4:
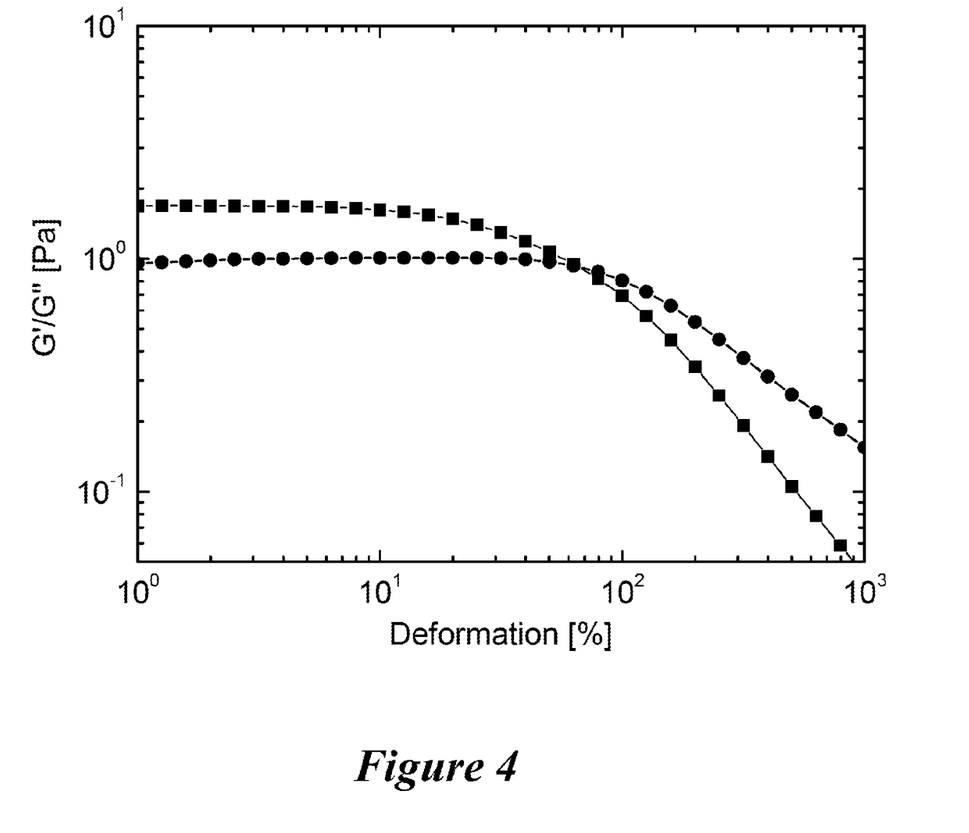
FIG. 4 is a graph showing storage modulus G' (-■-) and loss modulus G" (-●-) of a 1% strength solution in 100 g/l of NaCl water of TRIS[—CH$_2$—CH$_2$—O)$_{11}$H]$_2$[(—CH$_2$—CH$_2$—O)$_{11}$—SO$_3$Na] as a function of the deformation at a radian frequency of 10 rad s$^{-1}$.
Figure 5:
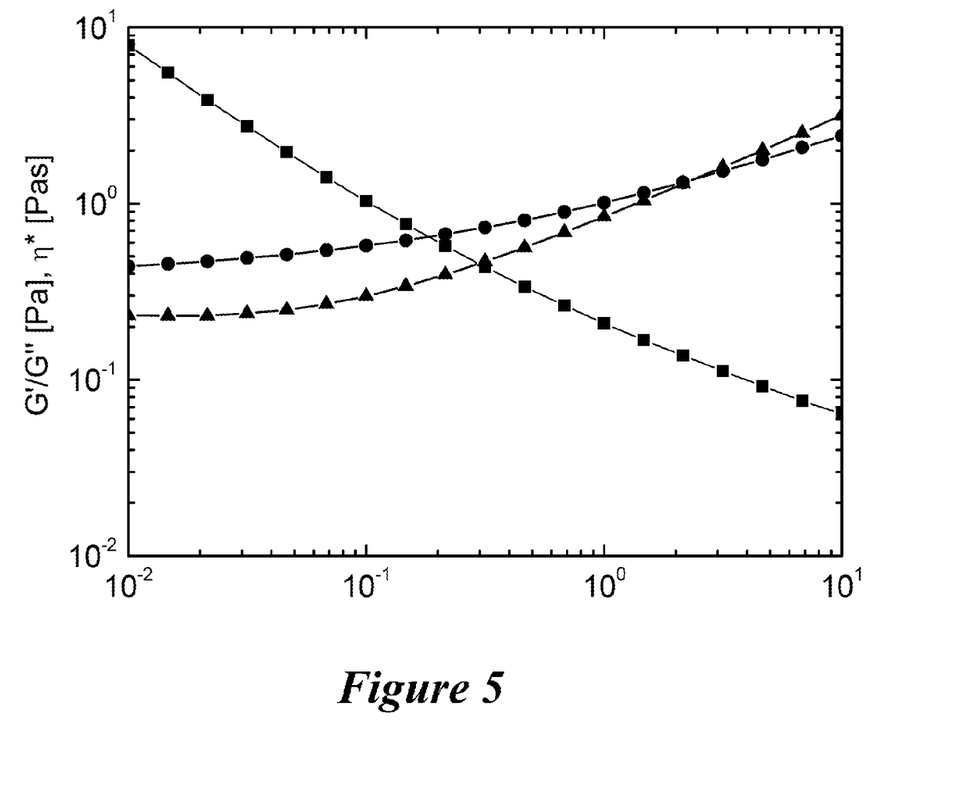
FIG. 5 is a graph showing storage modulus G' (-●-), loss modulus G" (-▲-) and complex viscosity η* (-■-) of a 1% strength solution in 100 g/l of NaCl water of TRIS[(—CH$_2$—CH$_2$—O)$_{11}$H]$_2$[(—CH$_2$—CH$_2$—O)$_{11}$—SO$_3$Na] as a function of the frequency at a constant deformation of 5%.

The results of the rheological investigations on TRIS[(—CH$_2$—CH$_2$—O)$_{11}$H]$_2$[(—CH$_2$—CH$_2$—O)$_{11}$—SO$_3$Na] are summarized in FIGS. 4 and 5. These characterize the viscoelastic properties of the sample (storage modulus and loss modulus) on the one hand as a function of the deformation and on the other hand as a function of the frequency of an oscillatory deformation.

Interfacial Activity of TRIS[(—CH$_2$—CH$_2$—O)$_{11}$H]$_2$[(—CH$_2$—CH$_2$—O)$_{11}$—SO$_3$Na]

The surface tension in completely demineralized water is 32.3 mN/m (1 g/l, 25° C.).

The interfacial tension between completely demineralized water and hexadecane is 6.9 mN/m (c=1 g/l; t=10 min, T=25° C.). Stable micelles can be inferred from the low dynamics.

Investigation Series 3:

Investigation of TRIS[(—CH$_2$—CH$_2$—O)$_{14}$H]$_3$

Figure 6:
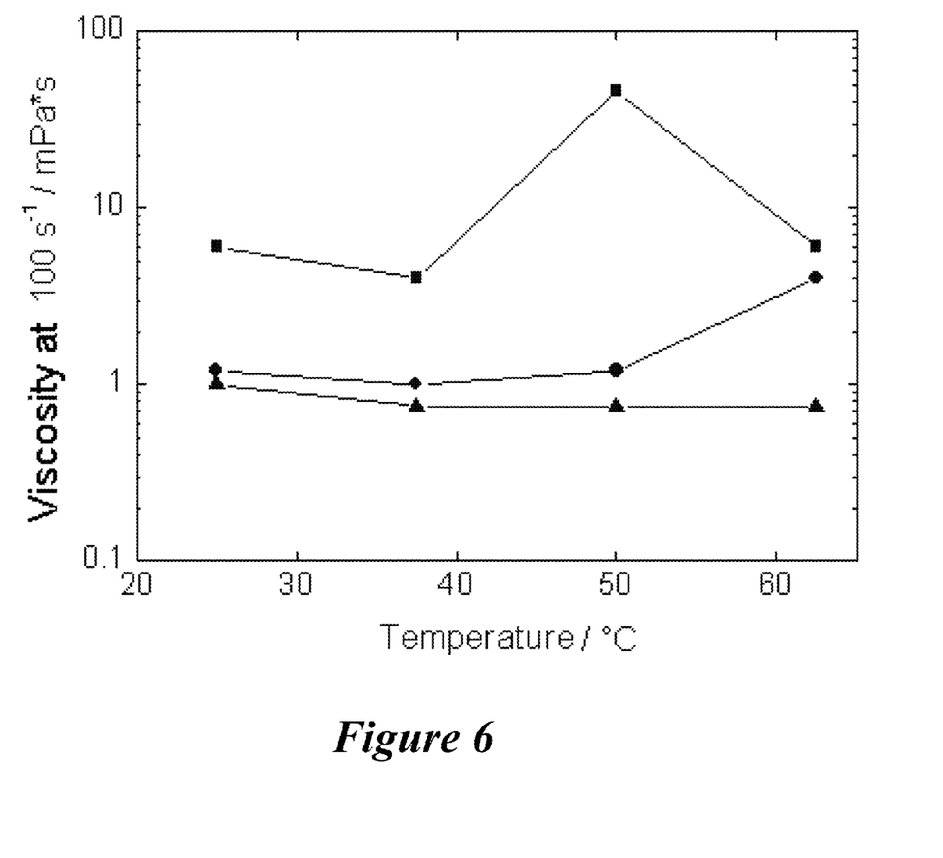
FIG. 6 is a graph showing viscosities as a function of the temperature of a 1% strength solution of TRIS[(—CH$_2$—CH$_2$—O)$_{14}$H]$_3$ in demineralized water (-▲-), water with 93 g/l (-●-) and 185 g/l (-■-) of dissolved salts (shear rate= 10 s$^{-1}$).

The results of the rheological investigations on TRIS[(—CH$_2$—CH$_2$—O)$_{14}$H]$_3$ (synthesized analogously to Synthesis Example 2, only with 42 instead of 33 EO units) are shown in FIG. 6. It can be seen that the viscous properties of the sample are in part increased as a result of the effect of salt and temperature.

Interfacial Activity of TRIS[(—CH$_2$—CH$_2$—O)$_{14}$H]$_3$

The surface tension in completely demineralized water is 34.8 mN/m (1 g/l, 25° C.).

The interfacial tension between completely demineralized water and hexadecane is 6.4 mN/m (t=10 min, T=25° C.). Stable micelles can be inferred from the low dynamics (measurement of the dynamic surface tension).

Investigation Series 4:

Investigation of the Substitution Pattern on the Aromatic

The surface tension and the interfacial tension against hexadecane of 0.1% strength by weight aqueous solutions of compounds according to the invention with different substitution patterns on the phenyl rings were investigated, specifically of the following compounds:

TRIS[(—CH$_2$—CH$_2$—O)$_{11}$H]$_3$      A

TRIS[(—CH$_2$—CH$_2$—O)$_{14}$H]$_3$      B

TRIS[(—CH$_2$—CH$_2$—O)$_{11}$H]$_2$[(—CH$_2$—CH$_2$—O)$_{11}$—SO$_3$Na]      C The different substituents $R^3$ and $R^4$ and also the results are summarized in Table 4. $R^1$ is always H.

TABLE 4

| | | | Surface tension [mN/m] | | Interfacial tension for hexadecane/water |
|---|---|---|---|---|---|
| Type | $R^3$ | $R^4$ | Du Nouy ring | Dynamics (1 s) | [mN/m] |
| A | H | H | 57 | 62 | 19.6 |
| A | methyl | methyl | 48 | 62 | 12.8 |
| A | t-butyl | t-butyl | 33 | 60 | 5.4 |
| B | t-butyl | t-butyl | 35 | 58 | 6.4 |
| C | t-butyl | t-butyl | 32 | 68 | 6.9 |

The results show that the substitution pattern on the phenyl rings has a large influence on the surfactant properties and on the viscoelasticity of the compounds according to the invention.

The molecule unsubstituted on the aromatic has only extremely low interfacial activity. The compound substituted with methyl groups has low interfacial activity whereas the product substituted with t-butyl groups has a high interfacial activity.

The interfacial activity can thus be adjusted in a simple manner for the compounds according to the invention.

The invention claimed is:

1. A derivative of tris(2-hydroxyphenyl)methane, wherein the tris(2-hydroxyphenyl)methane derivative has the general formula (I):

(I)

where the radicals $R^1$, $R^2$ and R have the following meaning:

R: are independently of one another, 0 to 4 $C_1$- to $C_{30}$-hydrocarbon radicals per phenyl ring, $R^1$: is a radical selected from the group consisting of H, OH, F, Cl, Br, I and $C_1$- to $C_{30}$-hydrocarbon groups, $R^2$: are independently of one another, radicals of the general formula —$(R^5$—O—$)_n$—$R^6$—X (III), where n is a number from 1 to 50, and where the radicals $R^5$, independently of one another, are selected from the group consisting of radicals $R^7$, $R^8$ and $R^9$ where $R^6$, X, $R^{10}$ and $R^{11}$, independently of one another, have the following meaning:

$R^6$: is a single bond or an alkylene group having 1 to 10 carbon atoms which can have optionally functional groups as substituents,

X: is H or an acidic group or a radical which comprises at least one OH group, $R^{10}$: is H or a $C_1$- to $C_6$-hydrocarbon radical, $R^{11}$: is a group —$(R^5$—O—$)_m$—$R^6$—X, where m is a number from 0 to 50, and where the total number z of all groups $R^5$ in a radical $R^2$ is 1 to 50, with the proviso that z is a number from 2 to 50, if at least one X is H.

2. The compound according to claim 1, wherein the compound has the general formula (II):

(II)

where $R^1$ and $R^2$ have the meaning given above and $R^3$ and $R^4$, independently of one another, are H or a $C_1$- to $C_{30}$-hydrocarbon radical.

3. The compound according to claim 2, wherein $R^3$ and $R^4$, independently of one another, are straight-chain or branched aliphatic $C_1$- to $C_6$-hydrocarbon radicals.

4. The compound according to claim 2, wherein $R^3$ and $R^4$ are in each case t-butyl radicals.

5. The compound according to claim 1, wherein z is a number from 5 to 30.

6. The compound according to claim 1, wherein X is an acidic group selected from the group consisting of carboxyl groups —COOM, sulfonic acid groups —$SO_3M$, sulfate groups —$OSO_3M$, phosphonic acid groups —$PO_2M_2$ or phosphoric acid groups —$OPO_3M_2$, where M is $H^+$ or a monovalent counterion.

7. The compound according to claim 1, wherein X is mono- or oligosaccharide radicals.

8. The compound according to claim 1, wherein at least one of the radicals $R^5$ is a radical $R^7$, where the radicals $R^{10}$ in $R^7$, independently of one another, are H, methyl or ethyl.

9. The compound according to claim 8, wherein at least 50% of the radicals $R^{10}$ are H.

10. The compound according to claim 1, wherein the radicals $R^2$, independently of one another, are radicals of the general formula —$(R^7$—O—$)_n$—$R^6$—X (IIIa), where the radicals $R^{10}$ in $R^7$, independently of one another, are selected from the group consisting of H, methyl or ethyl, with the proviso that at least 50% of the radicals $R^{10}$ are H and where n is a number from 5 to 30.

11. The compound according to claim 1, wherein the radicals $R^2$, independently of one another, are radicals of the general formula —$(R^7$—O—$)_n$—H (IIIb), where the radicals $R^{10}$ in $R^7$, independently of one another, are selected from the group consisting of H, methyl or ethyl, with the proviso that at least 50% of the radicals $R^{10}$ are H and where n is a number from 5 to 30.

12. The compound according to claim 1, wherein the radicals $R^2$, independently of one another, are radicals of the general formula —(—$CH_2$—$CH(R^{12})$—O—$)_a$—(—$CH_2$—$CH_2$—O—$)_b$—H (IIIc), where the alkylene oxide blocks are arranged in this order, $R^{12}$ is hydrocarbon radicals having 1 to 6 carbon atoms and a and b are in each case numbers from 1 to 49, with the proviso that the sum of a and b is 2 to 50.

13. The compound according to claim 1, wherein the group X is carboxyl groups —COOM, sulfonic acid groups —$SO_3M$ or sulfate groups —$OSO_3M$, where M is $H^+$ or a monovalent counterion.

14. The compound according to claim 1, wherein the radical of the general formula (III) comprises radicals $R^8$ and/or $R^9$.

15. A process for the preparation of the compounds according to claim 1, wherein a starting compound of the general formula (IV)

(IV)

is prepared, alkoxylated with reagents selected from the group consisting of $C_2$- to $C_8$-alkylene oxides, glycidol and cyclic $C_3$- to $C_9$-carbonates, and then optionally the terminal H atoms are substituted at least partially by radicals —$R^6$—X.

16. A surfactant or thickener which comprises the compound according to claim 1.

17. An article which comprises the compound according to claim 1, wherein the article is a detergent or cleaner, a paint or coating, a cosmetic or pharmaceutical formulation, paper, a textile or leather auxiliary, a formulation for human and animal nutrition, a construction material, a formulation for crop protection, or a material for producing emulsions and dispersions.

18. The derivative of tris(2-hydroxyphenyl)methane according to claim 1, wherein X is a radical which comprises at least two OH groups.

* * * * *